(12) United States Patent
Wu

(10) Patent No.: US 10,216,007 B2
(45) Date of Patent: Feb. 26, 2019

(54) CONTACT LENS HAVING A MOIRÉ STRUCTURE, CONTACT LENS MOIRÉ STRUCTURE PROCESSING METHOD

(71) Applicant: BRIGHTEN OPTIX CORP., Taipei (TW)

(72) Inventor: I-Tsung Wu, Taipei (TW)

(73) Assignee: BRIGHTEN OPTIX CORP., Taipei (TW)

( * ) Notice: Subject to any disclaimer, the term of this patent is extended or adjusted under 35 U.S.C. 154(b) by 62 days.

(21) Appl. No.: 15/207,791

(22) Filed: Jul. 12, 2016

(65) Prior Publication Data

US 2018/0017810 A1  Jan. 18, 2018

(51) Int. Cl.
| | |
|---|---|
| *G02C 7/04* | (2006.01) |
| *G02B 27/60* | (2006.01) |
| *A61B 3/10* | (2006.01) |
| *A61B 3/00* | (2006.01) |
| *G02C 7/02* | (2006.01) |

(52) U.S. Cl.
CPC ............ *G02C 7/044* (2013.01); *A61B 3/0025* (2013.01); *A61B 3/1015* (2013.01); *G02B 27/60* (2013.01); *G02C 7/024* (2013.01); *G02C 7/041* (2013.01); *G02C 2202/24* (2013.01)

(58) Field of Classification Search
CPC .... G02C 7/044; G02C 2202/24; G02B 27/60; A61B 3/0025; A61B 3/1015
See application file for complete search history.

(56) References Cited

U.S. PATENT DOCUMENTS 8,169,716 B2 * 5/2012 Zalevsky ............. G02B 5/1895
216/26

* cited by examiner

*Primary Examiner* — Jack Dinh
(74) *Attorney, Agent, or Firm* — Muncy, Geissler, Olds & Lowe, P.C.

(57) ABSTRACT

Contact lens includes central optical zone for clearly focusing image of incident light onto retina clear central image region of user's eyeball and peripheral optical zone surrounding central optical zone, and one or multiple moiré portions located on peripheral optical zone for focusing the image of incident light onto peripheral out-of focus region of retina of user's eyeball. The moiré portions are processed by: using an aberrometer to measure aberration of retina of user's eyeball and to further generate a three-dimensional image map, dividing the three-dimensional image map into clear central image region and peripheral out-of focus region, and then using an aberration correction software to calculate the power of sphere and the power and axis of cylinder on contact lens and then inputting the three-dimensional image map into processing machine for enabling the processing machine process the desired moiré portions on contact lens according to the three-dimensional image map.

3 Claims, 6 Drawing Sheets

CONTACT LENS HAVING A MOIRÉ STRUCTURE, CONTACT LENS MOIRÉ STRUCTURE PROCESSING METHOD

BACKGROUND OF THE INVENTION

1. Field of the Invention

The present invention urelates to contact lens processing technology and more particularly, to a contact lens that has at least one moiré portion in the peripheral optical zone around the central optical zone for interfering with incident light to change the focal point of the imaging light on the retina of the user's eyeball, so as to effectively slow or prevent increasing in refractive error and correct myopia.

2. Description of the Related Art

The development of innovative Computers/Communications/Consumers products have made life easier and more convenient. Especially the creation of a large number of 3C products results in the popularity of communication and Internet applications. However, many people immerse themselves in the use of 3C electronic products. Mobile phone overuse is seen among certain office workers, students, middle aged and elderly people. Some mobile phone users exhibit problematic behaviors related to substance use disorders. Mobile phone overuse can also lead to visual impairment, injury, and increase in myopia prevalence.

However, in order to correct myopia, also known as near-sightness and short-lightness, you may need to wear glasses or contact lenses. Eyeglasses or contact lenses have the opposing inner and outer surfaces thereof configured to provide different curvatures so that the central optical zone can focus a clear image of the incident light on the fovea in the user's eyeball, and the peripheral optical zone around the central optical zone can focus the image of the incident light on the peripheral out-of focus region of the retina in the user's eyeball. Peripheral refraction is less than central refraction, and peripheral myopic defocus can slow or prevent increasing in refractive error and correct myopia. However, the peripheral optical zones of glasses and contact lenses provide only one single curvature. Because human's eye and retina are not absolutely regular, peripheral image may focus behind the retina. Therefore, it is desirable to provide a contact lens with a special design on the peripheral optical zone to fit the eyeballs of most people for effectively slowing or preventing increasing refractive error and correct myopia.

SUMMARY OF THE INVENTION

The present invention has been accomplished under the circumstances in view. It is therefore the main object of the present invention to provide a contact lens that comprises opposing outer surface and inner surface, a central optical zone located on the outer surface and the inner surface for the passing of light to focus a clear image on a clear central image region of a retina of a user's eyeball, a peripheral optical zone located on the outer surface of the inner surface and surrounding the central optical zone, and at least one moiré portion located on the peripheral optical zone for the passing of light to focus an image on a peripheral out-of focus region of the retina of the user's eye. Thus, at least one moiré portion interferes with incident light to change the focal point of the incident light on the retina of the user's eyeball, thereby effectively slowing or preventing increasing refractive error and correct myopia.

It is another object of the present invention to provide a contact lens moiré structure processing process that includes the step of: using an aberrometer to measure the aberration of a retina of a user's eyeball and to further generate a three-dimensional image map, the step of dividing the three-dimensional image map into a clear central image region and a peripheral out-of focus region, and the step of using an aberration correction software to calculate the power of sphere and the power and axis of cylinder on contact lens and then inputting the three-dimensional image map into a processing machine and process the desired moiré portions on a contact lens according to the three-dimensional image map.

Other advantages and features of the present invention will be fully understood by reference to the following specification in conjunction with the accompanying drawings, in which like reference signs denote like components of structure.

DETAILED DESCRIPTION OF THE PREFERRED EMBODIMENT

Figure 1:
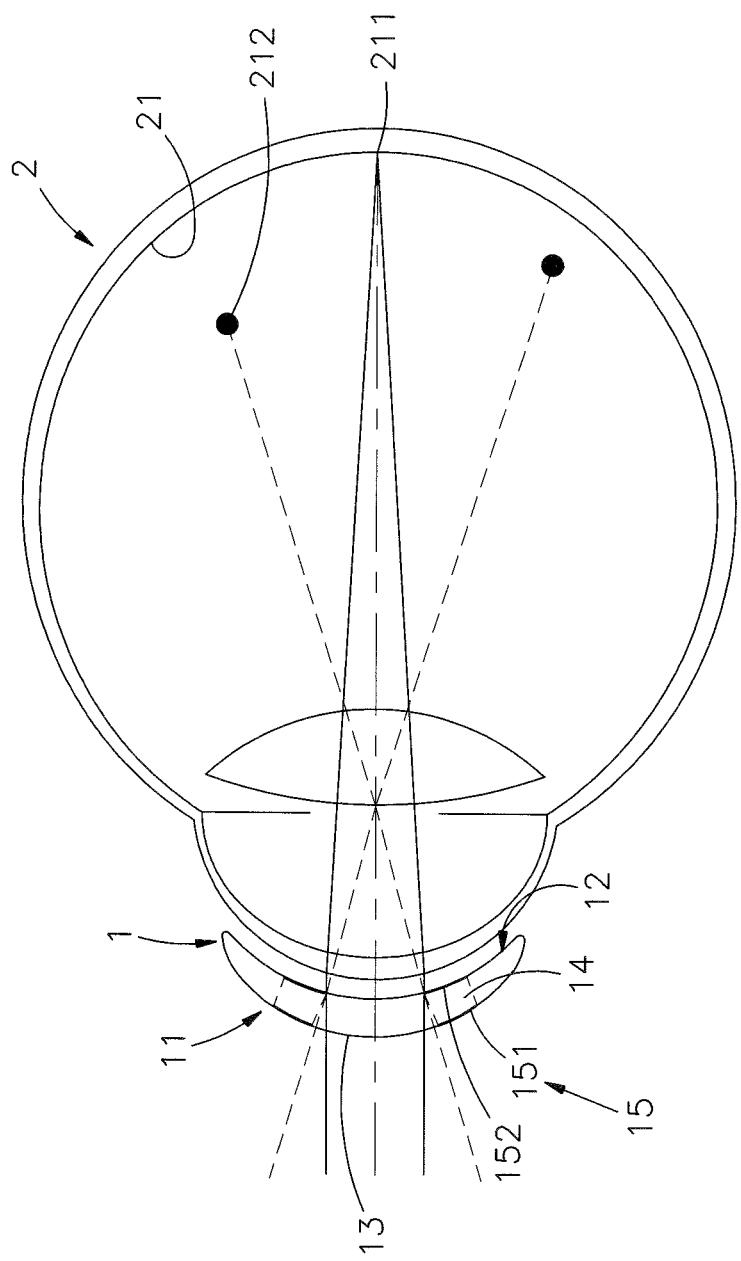
FIG. 1 is a schematic drawing illustrating the path of light passed through a contact lens and the user's eyeball in accordance with the present invention.
Figure 2:
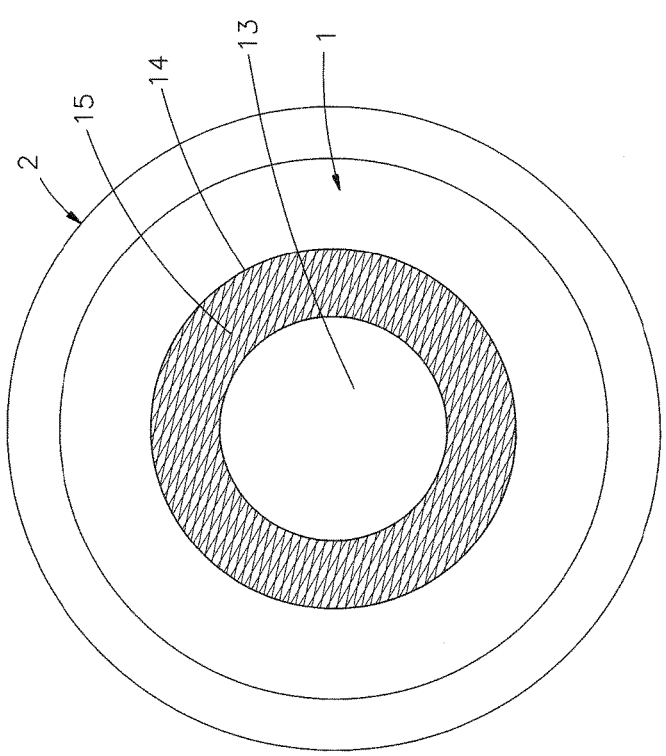
FIG. 2 is a schematic plain view of the present invention, illustrating one moiré portion located on the peripheral optical zone around the central optical zone of the contact lens in accordance with the present invention.
Figure 3:
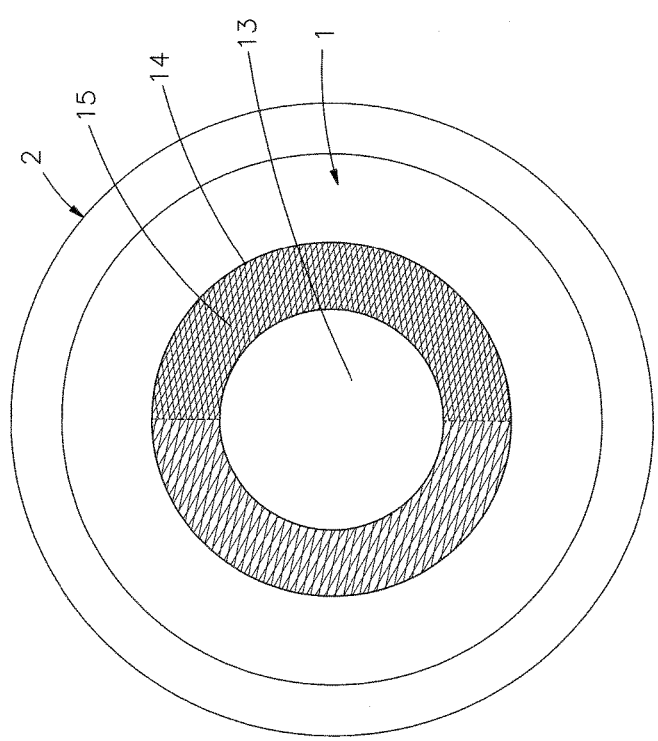
FIG. 3 is a schematic plain view of the present invention, illustrating two moiré portions located on the peripheral optical zone around the central optical zone of the contact lens in accordance with the present invention.

Referring to FIGS. 1, 2 and 3, contact lens, referenced by 1, comprising an outer surface 11, an opposing inner surface 12, a central optical zone 13 located on the outer surface 11 and the inner surface 12 for the passing of light to focus a clear image on a clear central image region 211 of a retina 21 of a user's eyeball 2, a peripheral optical zone 14 surrounding the central optical zone 13, and at least one moiré portion 15 located on the peripheral optical zone 14 for the passing of light to focus an image on a peripheral out-of focus region 212 of the retina 21 of the user's eyeball 2. Each the moiré portion 15 comprises a first pattern 151 and a second pattern 152 respectively located on the outer surface 11 and the inner surface 12 and respectively formed of a respective grating that is a regularly spaced collection of essentially identical, parallel, elongated elements.

In one embodiment of the present invention, as shown in FIG. 2, the one single moiré portion 15 is located on the peripheral optical zone 14 in a three hundred and sixty degrees full coverage manner. In another embodiment of the present invention, as shown in FIG. 3, the two moiré portions 15 are located on the peripheral optical zone 14 and connected to each other to achieve three hundred and sixty degrees full coverage. Alternatively, the contact lens 1 can be configured to provide the one single moiré portion 15 located on the peripheral optical zone 14 in a ninety degrees, one hundred eighty degrees or two hundred seventy degrees partial coverage manner, or alternatively, the contact lens 1 can be configured to provide a plurality of the moiré portions 15 located on the peripheral optical zone 14 and spaced from one another through three hundred and sixty degrees. In general, the pattern and at least the one moiré portion 15 in the peripheral optical zone 14 can be determined subject to the shape of the retina 21 of the user's eyeball 2 for focusing images on the peripheral out-of focus region 212.

Further, it is to be noted that the grating of each the moiré portion 15 is an optical component of a regularly spaced collection of essentially identical, parallel, elongated elements for enabling the amplitude and/or phase of the incident light to be periodically modulated.

Figure 4:
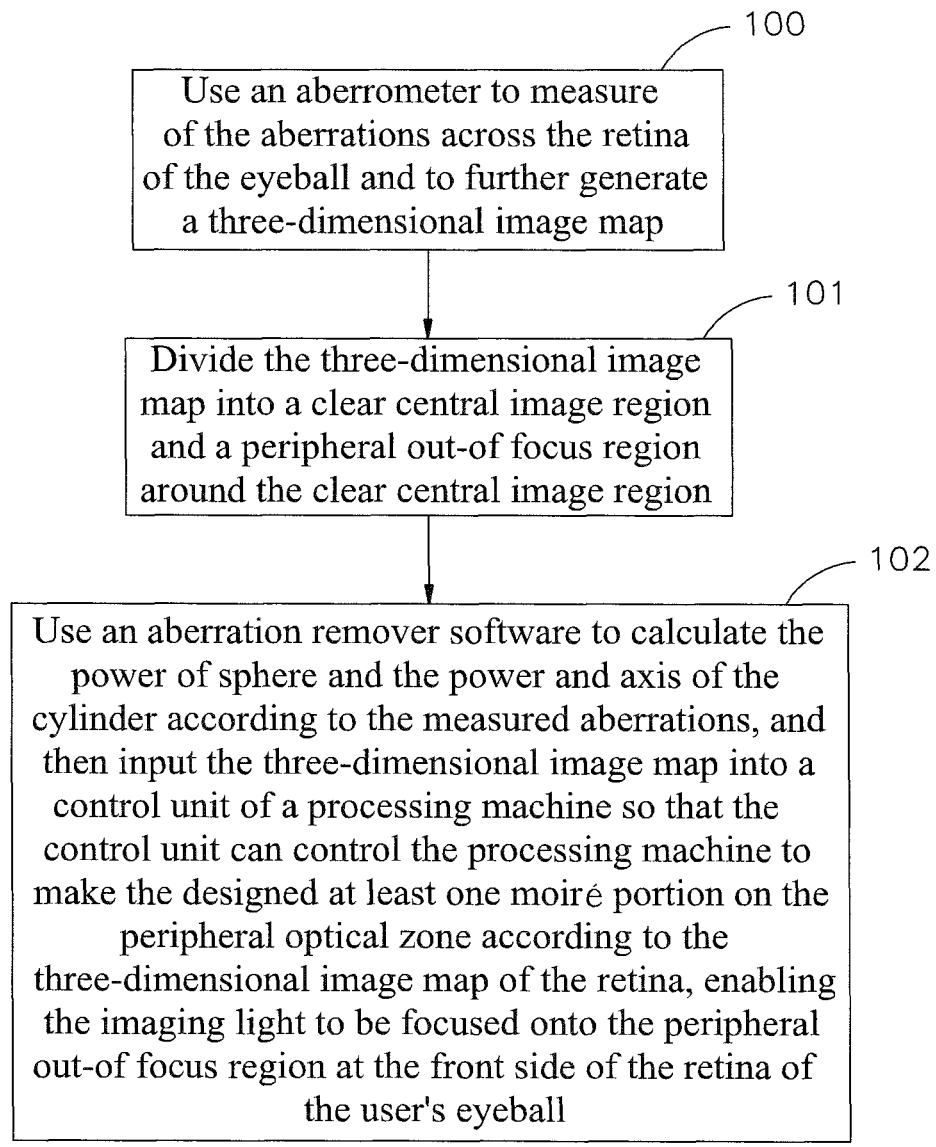
FIG. 4 is a contact lens moiré structure processing flow in accordance with the present invention.

Referring to FIG. 4 and FIGS. 1-3 again, the retina 21 of the eyeball 2 of an ordinary person exhibits an irregular shape, i.e., the distance between the peripheral optical zone 14 of the contact lens 1 and the retina 21 will be more difficult to predict, however, an aberrometer can be used to measure the aberrations across the retina 21 of the user's eyeball 2 and to further generate a three-dimensional image map, and then this three-dimensional image map is divided into the clear central image region 211 and the peripheral out-of focus region 212 around the clear central image region 211. Thereafter, an aberration correction software is used to calculate the power of sphere and the power and axis of cylinder on contact lens according to the measured aberrations, and then the three-dimensional image map is inputted into a control unit of a processing machine, and then the processing machine is controlled by the control unit to make the first pattern 151 and the second pattern 152 of the designed at least the one moiré portion 15 on the outer surface 11 and the inner surface 12 in the peripheral optical zone 14 according to the three-dimensional image map of the retina 21. The superimposition of the first pattern 151 and the second pattern 152 at least the one moiré portion 15 will interfere with the light passing therethrough to change the focal position of the imaging light on the retina 21 of the user's eyeball 2, so that the incident light can be focused onto the peripheral out-of focus region 212 at the front side of the retina 21 of the user's eyeball 2, providing a same degree of out-of-focus image in peripheral vision in line with the shape of the retina 21 of the user's eyeball 2, so as to effectively slow or prevent increasing refractive error and correct myopia.

Figure 5:
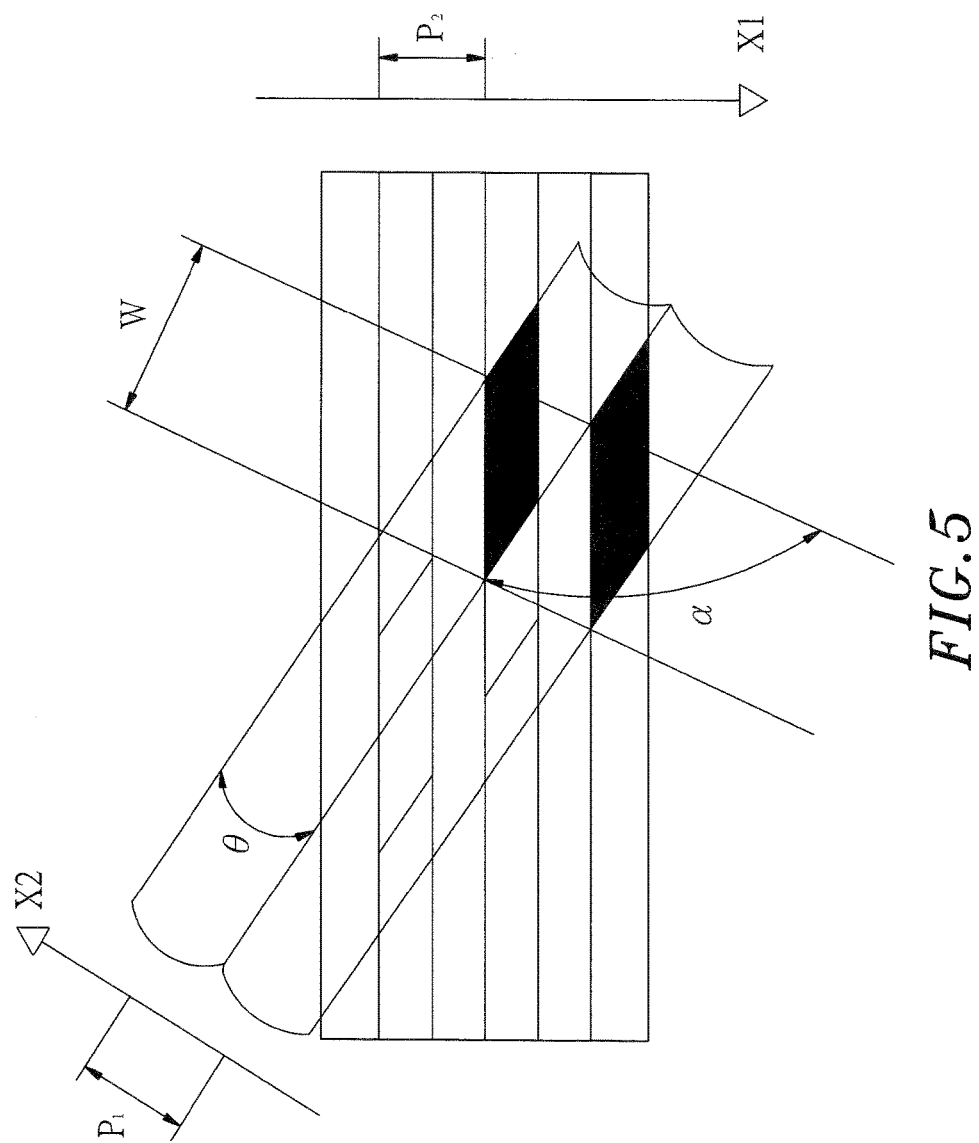
FIG. 5 is a schematic drawing illustrating the superimposition of two patterns of one moiré portion in accordance with the present invention.

Further, the first pattern 151 and the second pattern 152 of each the moiré portion 15 can be the same transparent grating or grid design, or different transparent grating or grid designs, and superimposed to interfere with the light passing therethrough. Further, the focal point of the incident light to be focused onto the peripheral out-of focus region 212 at the front side of the retina 21 of the user's eyeball 2 can be adjusted by means of changing the spacing between the grating or grid of the first pattern 151 and the grating or grid of the second pattern 152 and the distance between the first pattern 151 and the second pattern 152 (i.e., the thickness of the peripheral optical zone 14). Simply by means of fitting the upper and lower surfaces to form a moiré structure, the available range of values for calculation in the processing process is very small and has limitations. It is observed that changing the angle of the first pattern 151 and the angle of the second pattern 152 will cause a change in the moiré pattern, and the moiré will be relatively smaller when the angle is relatively increased. The calculation can be done through the following formula (see FIG. 5):

$$W = P_1 P_2 / \sqrt{P_1^2 + P_2^2 - 2P_1 P_2 \cos\theta}$$

In which: W: image size for the moiré portion 15; P1: the size of the first pattern 151; P2: the size of the second pattern 152; θ: the contained angle between the first pattern 151 and the second pattern 152.

Through the calculation of the aforesaid mathematical formula, at least the one moiré portion 15 thus made can accurately focus the image of the light passing therethrough onto the peripheral out-of focus region 212 at the front side of the retina 21 of the user's eyeball 2.

Further, the aforesaid processing machine can be, for example, a printing press for printing gratings on the contact lens 1 by means of lithographic printing or UV ink screen printing. In actual practice, an ultra-precision lathe for non-rotationally symmetric lens machine can be used as a substitute for printing gratings on the contact lens 1 to form the designed at least the one moiré portion 15. Various different types and models of printing presses for printing gratings on contact lenses are commercially available. However, the basic structure and processing methods vary depending on the scope of applications. As the detailed compositions of the related processing machines are not within the scope of the present invention, no further detailed description will be necessary.

Further, it should be noted that, in an ideal optical system, all rays of light from a point in the object plane would converge to the same point in the retina, forming a clear image. Aberrations are the influences which cause different rays to converge to different points.

Aberrometer is a diagnostic device that measures aberrations of the eye. It is a diagnostic tool used to identify aberrations that allows physicians to differentiate between traditional refractive errors such as myopia, astigmatism, and higher order aberrations, such as coma, trefoil aberration and spherical aberration.

Referring to FIGS. 1 and 2 again, the power of the peripheral optical zone 14 of the contact lens 1 is relatively lower (more plus) than the central optical zone 13, i.e, when the user wants to correct myopia, the imaging distance of the user's eyeball 2 before being corrected is too short. After the user wears the contact lens 1, the image of the light passing through the central optical zone 13 will be focused onto the retina 21, and the image of the light passing through the peripheral optical zone 14 will be focused onto the peripheral out-of focus region 212 at the front side of the retina 21 to control myopia.

Referring to FIGS. 1-4 again when machining the contact lens 1, the processing method is performed subject to the steps as follows:

(100) Use an aberrometer to measure of the aberrations across the retina 21 of the eyeball 2 and to further generate a three-dimensional image map.

(101) Divide the three-dimensional image map into the clear central image region 211 and the peripheral out-of focus region 212 around the clear central image region 211.

(102) Use an aberration correction software to calculate the power of sphere and the power and axis of cylinder on contact lens according to the measured aberrations, and then input the three-dimensional image map into a control unit of a processing machine so that the control unit can control the processing machine to make the designed at least the one moiré portion 15 on the peripheral optical zone 14 according to the three-dimensional image map of the retina 21, where at least the one moiré portion 15 can interfere with the light passing therethrough to change the focal position of the imaging light on the retina 21 of the user's eyeball 2, so that the imaging light can be focused onto the peripheral out-of focus region 212 at the front side of the retina 21 of the user's eyeball 2.

Figure 6:
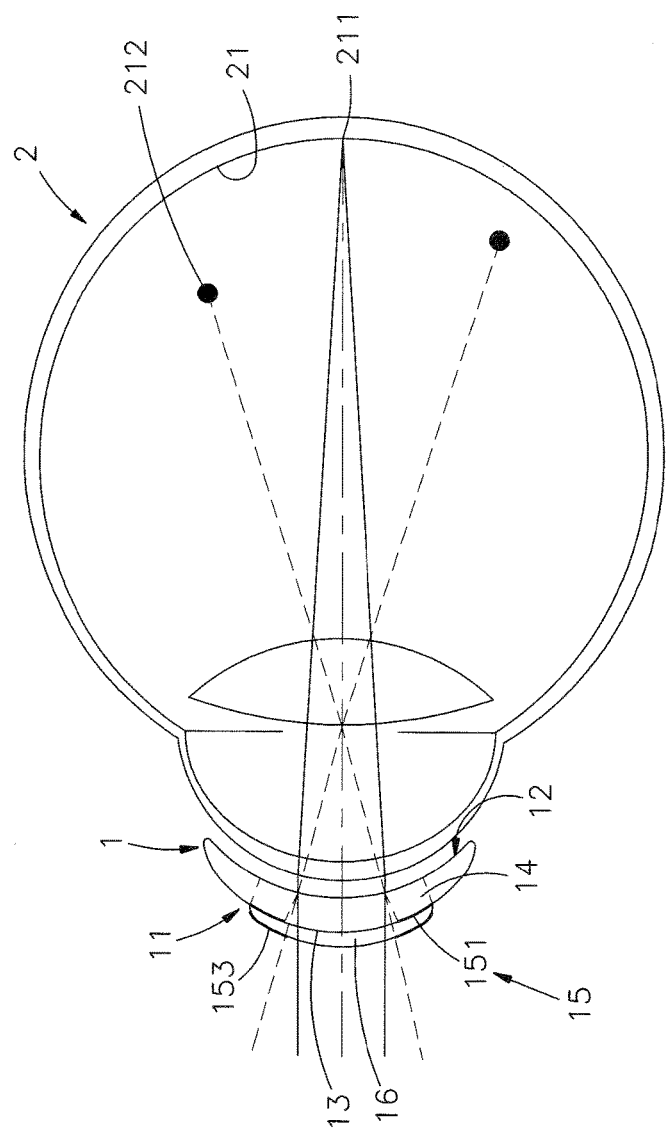
FIG. 6 is a schematic drawing illustrating the path of light passed through an alternate form of the contact lens and the user's eyeball in accordance with the present invention.

Referring to FIG. 6 and FIG. 1 again, in an alternate form of the present invention, the contact lens 1 eliminates the second pattern 152 from each the moiré portion 15; and has a light-transmitting material layer 16 located on the outer surface 11 of the contact lens 1, and a third pattern 153 located on an outer surface of the light-transmitting material layer 16 opposite to the outer surface 11 of the contact lens 1. This the third pattern 153 is superimposed on the associated first pattern 151 to form a moiré pattern that will interfere with the light passing therethrough to change the focal position of the imaging light on the retina 21 of the user's eyeball 2. Thus, the imaging light can be focused onto the peripheral out-of focus region 212 at the front side of the retina 21 of the user's eyeball 2 to effectively slow or prevent increasing refractive error and to correct myopia.

Further, the light-transmitting material layer 16 can be adhered to the overall area of the outer surface 11 of the contact lens 1. The curvature and size of the light-transmitting material layer 16 are determined subject to curvature and size of the outer surface 11. In an alternate form of the present invention, the light-transmitting material layer 16 can be adhered to a part of the outer surface 11 of the contact lens 1 to simply cover the peripheral optical zone 14 of the contact lens 1. Many known methods and tools can be selectively used for making gratings or grids of the desired at least the one moiré portion 15 on the contact lens 1, so that two patterns can be superimposed to create a moiré pattern.

Further, the first pattern 151 of the moiré portion 15 and the third pattern 153 on the light-transmitting material layer 16 can configured to provide one same transparent grating or grid design, or different transparent grating or grid designs. Further, the focal point of the imaging light to be focused onto the peripheral out-of focus region 212 at the front side of the retina 21 of the user's eyeball 2 can be adjusted by means of changing the spacing between the grating or grid of the first pattern 151 and the grating or grid of the third pattern 153 and the distance between the first pattern 151 and the third pattern 153 (i.e., the thickness of the light-transmitting material layer 16).

In conclusion, the invention provides a contact lens 1 that comprises at least one moiré portion 15 located on a peripheral optical zone 14 around a central optical zone 13 for interfering with the light passing therethrough to change the focal position of the imaging light on a retina 21 of a user's eyeball 2, so as to effectively slow or prevent increasing refractive error and correct myopia.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A contact lens, comprising opposing outer surface and inner surface, a central optical zone located on said outer surface and said inner surface for the passing of light to focus a clear image on a clear central image region of a retina of a user's eyeball, a peripheral optical zone located on said outer surface and said inner surface and surrounding said central optical zone, and at least one moiré portion located on said peripheral optical zone for the passing of light to focus an image on a peripheral out-of focus region of said retina of said user's eyeball;

wherein each said moiré portion comprises a first pattern and a second pattern respectively located on said outer surface and said inner surface and superimposed to form a moiré pattern, said first pattern and said second pattern each being respectively formed of a respective grating that is a regularly spaced collection of essentially identical, parallel, elongated elements.

2. The contact lens as claimed in claim 1, wherein each said moiré portion comprises said first pattern located on said outer surface of said contact lens, a light-transmitting material layer located on said outer surface of said contact lens, and a third pattern located on said outer surface of said light-transmitting material layer opposite to said first pattern and superimposed on said first pattern to form a moiré pattern, said first pattern and said third pattern each being respectively formed of a respective grating that is a regularly spaced collection of essentially identical, parallel, elongated elements.

3. The contact lens as claimed in claim 1, wherein said at least one moiré portion is located on said peripheral optical zone in one of ninety degrees, one hundred and eighty degrees, two hundred and seventy degrees and three hundred and sixty degrees.

* * * * *